(12) United States Patent
Grondin et al.

(10) Patent No.: US 10,758,204 B2
(45) Date of Patent: Sep. 1, 2020

(54) RADIOGRAPHIC IMAGING SYSTEM AND METHOD FOR POSITIONING ONE SUCH SYSTEM

(71) Applicants: UNIVERSITÉ GRENOBLE ALPES, Saint-Martin-D'Hères (FR); SURGIQUAL INSTITUTE, Meylan (FR); CENTRE HOSPITALIER UNIVERSITAIRE GRENOBLE ALPES, La Tronche (FR)

(72) Inventors: Yannick Grondin, Challes les Eaux (FR); Philippe Augerat, Saint-Ismier (FR); Philippe Cinquin, St Nazaire les Eymes (FR); Laurent Desbat, La Tronche (FR); Benjamin Spencer, Grenoble (FR)

(73) Assignees: UNIVERSITÉ GRENOBLE ALPES, Saint-Martin-D'Hères (FR); SURGIQUAL INSTITUTE, Meylan (FR); CENTRE HOSPITALIER UNIVERSITAIRE DE GRENOBLE ALPES, La Tronche (FR)

( * ) Notice: Subject to any disclaimer, the term of this patent is extended or adjusted under 35 U.S.C. 154(b) by 458 days.

(21) Appl. No.: 15/524,942

(22) PCT Filed: Nov. 5, 2015

(86) PCT No.: PCT/FR2015/052998
§ 371 (c)(1),
(2) Date: May 5, 2017

(87) PCT Pub. No.: WO2016/071645
PCT Pub. Date: May 12, 2016

(65) Prior Publication Data
US 2017/0332986 A1    Nov. 23, 2017

(30) Foreign Application Priority Data

Nov. 5, 2014  (FR) .................................... 14 60687

(51) Int. Cl.
*A61B 6/00* (2006.01)
*A61B 6/14* (2006.01)

(52) U.S. Cl.
CPC ............ *A61B 6/587* (2013.01); *A61B 6/4405* (2013.01); *A61B 6/4452* (2013.01); *A61B 6/588* (2013.01); *A61B 6/14* (2013.01); *A61B 6/4291* (2013.01)

(58) Field of Classification Search
CPC ....... A61B 6/14; A61B 6/4035; A61B 6/4291; A61B 6/4405; A61B 6/4452; A61B 6/587; A61B 6/588; G01N 23/04; G03B 42/02
See application file for complete search history.

(56) References Cited

U.S. PATENT DOCUMENTS

2002/0080922 A1   6/2002   Kwasnick et al.
2002/0150215 A1   10/2002  Barnes et al.
(Continued)

FOREIGN PATENT DOCUMENTS

FR   2 899 349 A1   10/2007
JP   2010-178914 A   8/2010

OTHER PUBLICATIONS

May 9, 2017 International Preliminary Report on Patentability issued with International Patent Application No. PCT/FR2015/052998.

*Primary Examiner* — Chih-Cheng Kao
(74) *Attorney, Agent, or Firm* — Oliff PLC (57) ABSTRACT

Radiographic imaging system including: an x-ray transmission unit; an x-ray receiver unit; a plate made from a material opaque to x-rays and situated between the trans-
(Continued)

mission unit and the receiver unit, the plate including at least four channels, each channel enabling a part of the x-rays emitted by the transmission unit to pass through the channel; and an image processing unit configured to determine the coordinates of the projected patterns and to calculate a position of the receiver unit from the coordinates of the projected patterns and from the coordinates of the channels.

17 Claims, 5 Drawing Sheets

(56) References Cited

U.S. PATENT DOCUMENTS

| | | |
|---|---|---|
| 2003/0163271 A1 | 8/2003 | Chell et al. |
| 2005/0201613 A1* | 9/2005 | Mostafavi ............... A61B 6/463 382/154 |
| 2006/0280293 A1 | 12/2006 | Hardesty |
| 2007/0122020 A1 | 5/2007 | Claus et al. |
| 2007/0223657 A1 | 9/2007 | Birdwell |
| 2009/0060145 A1 | 3/2009 | Tranchant et al. |
| 2011/0013752 A1* | 1/2011 | Takahashi ............... A61B 6/583 378/205 |
| 2011/0176663 A1 | 7/2011 | Shaughnessy |
| 2012/0230473 A1 | 9/2012 | Stagnitto et al. |
| 2013/0051528 A1 | 2/2013 | Inglese et al. |

\* cited by examiner

RADIOGRAPHIC IMAGING SYSTEM AND METHOD FOR POSITIONING ONE SUCH SYSTEM

BACKGROUND OF THE INVENTION

The invention relates to radiographic imaging, in particular x-ray imaging, and more particularly mobile radiographic imaging in the medical field, in particular the dental field.

STATE OF THE ART

Mobile radiographic systems are currently used to take radiographic images, in particular radiographic images at a patient's bedside. These mobile systems comprise an x-ray transmission unit and an x-ray receiver unit, and these equipment items are placed on each side of an object, such as a patient, a recipient, or any other object for which it is desired to obtain a radiographic image with a view to examining the object. These mobile systems are handled by an operator and can become misaligned, which can produce an image with contrast and/or deformation defects of the object. In this case, the image is difficult to use. Certain radiography systems propose means for aligning the transmission unit with the receiver unit.

American Patent applications US2012/0230473, US2013/0051528 and French Patent application FR2899349 can for example be cited, which disclose an x-ray radiographic imaging system using a magnetic positioning device comprising an electromagnetic wave transmitter located on the x-ray transmission unit and a wave receiver located on the receiver unit. But such systems require an electromagnetic wave transceiver device in addition to the x-ray transmission unit/receiver unit assembly, which makes the imaging system bulky.

Furthermore, the electromagnetic radiation of the positioning device can be disturbed by equipment located nearby.

American patent application US2002/0150215 discloses an x-ray imaging system using an optic, or ultrasonic, or magnetic camera, situated on the x-ray transmission unit and markers placed on the receiver unit. The camera produces an image of the markers in order to determine the position of the receiver unit. But the field of vision of an optic or ultrasonic camera can be obstructed by the object to be analysed. Furthermore, magnetic cameras can be disturbed by metallic objects located nearby.

American Patent application US2007/0223657 discloses a method for performing alignment of an x-ray transmitter and detector movable by motorized movement means. The method consists in placing the detector in an initial position and, by means of the detector, in generating a map, in one or more dimensions, of the radiation profile comprising regions of interest identifiable by their radiation intensity level. Then the detector is moved to other positions and the new radiation profiles and their coordinates in space are recorded. Once the radiation profile map has been obtained, it can be used to align the source and detector. But such a method requires a large number of radiographic images to be taken, and the detector has to be able to be moved along the radiation propagation axis, which is not always possible when the detector is placed under a patient's bed, in particular when taking a chest x-ray of a bedridden person.

American Patent application US2002/0080922 discloses an x-ray radiographic method using a receiver unit comprising an x-ray detector and an anti-scatter grid situated on the detector, the grid comprising pairs of alignment bars opaque to x-rays. In this method, a first image of the object is made with a radiation delivering a weak dose of x-rays, the relative position of the alignment bars in the first image is then measured, the relative angle of the detector with respect to the transmission unit is adjusted, and a second image is made with a radiation delivering a strong dose of x-rays, for a radiographic image. But this method requires the use of an anti-scatter grid situated on the detector, which is not always the case, in particular in dental radiology which uses intra-oral detectors not comprising a grid. Furthermore, in the case where the grid is focused, the method does not make it possible to determine the distance between the receiver unit and the transmission unit which then has to be equal to the focal distance of the grid.

American Patent application US2006/0280293 can also be cited which discloses a radiographic imaging system by x-ray using a reticle opaque to x-rays placed on the x-ray transmission unit. The reticle comprises one or more openings which let a part of the x-rays pass in order to obtain an image comprising the specific projection of a single pattern of the openings. Then the image is displayed by means of a readout screen and a distance between the edge of the pattern and the edge of the screen is measured in order to determine whether the receiver unit is centred with respect to the transmission unit. However, the document does not give any teaching on the x-ray dose delivered. Furthermore, the system only enables the receiver unit to be centered and does not provide the possibility of positioning the receiver unit precisely.

OBJECT OF THE INVENTION

One object of the invention consists in palliating the shortcomings set out above, and in particular in providing means for facilitating positioning of the receiver unit with respect to the transmission unit of an x-ray radiographic imaging system.

Another object is to limit the x-ray doses used when performing positioning of the receiver unit with respect to the transmission unit.

According to one feature of the invention, a radiographic imaging system is proposed comprising:
- an x-ray transmission unit;
- an x-ray receiver unit; and
- a plate made from a material opaque to x-rays and situated between the transmission unit and the receiver unit.

The plate comprises at least four channels, each channel enabling a part of the x-rays emitted by the transmission unit to pass through the channel; the receiver unit generates a radiographic alignment image comprising a projected pattern of each channel; and the system comprises an image processing unit configured to determine the coordinates of the projected patterns in the alignment image and to calculate a position of the receiver unit from the coordinates of the projected patterns in the alignment image and from the coordinates of the channels.

The image processing unit can further comprise a memory to store parameters of a first geometric transformation matrix respectively linking coordinates of the reference patterns with the coordinates of the channels, each reference pattern corresponding to a projection of a channel in a reference radiographic image generated when the receiver unit is located at a reference distance from the transmission unit, the processing unit being further configured to identify the projected pattern in the alignment radiographic image of each channel, to match the projected patterns in the alignment radiographic image respectively with the channels of the plate, to calculate parameters of a second geometric transformation matrix linking the coordinates of the projected patterns in the radiographic image with the coordinates of the reference patterns, and to calculate the position of the receiver unit from the parameters of the first and second matrices.

The plate can comprise several channels forming an asymmetric figure.

The plate can comprise at least two channels aligned along a first axis, at least two channels aligned along a second axis perpendicular to the first axis, and at least three channels aligned along a third axis inclined with respect to the first and second axes.

The transmission unit and receiver unit can be mobile.

A mobile radiographic imaging system is thus provided that it is particularly suitable for chest x-rays performed in a patient's bed and for dental radiography.

The channels can have a cylindrical shape.

The cross-sections of the channels can have different diameters from one another.

According to another feature, a method for positioning a radiographic imaging system is proposed comprising an x-ray transmission unit and an x-ray receiver unit, the method comprising the following steps:

arranging a plate made from a material opaque to x-rays between the transmission unit and the receiver unit, the plate comprising at least four channels, each channel enabling a part of the x-rays emitted by the transmission unit to pass through the channel;

emitting x-rays by the transmission unit;

generating, by the receiver unit, an alignment radiographic image comprising a projected pattern of each channel;

determining coordinates of the projected patterns in the alignment radiographic image; and calculating a position of the receiver unit from the coordinates of the projected patterns in the alignment radiographic image and from the coordinates of the channels.

The calculation step can further comprise a calibration step in which generating a reference radiographic image comprising a projected reference pattern of each channel, by the receiver unit situated at a reference distance from the transmission unit, determining the coordinates of the reference patterns, and calculating parameters of a first geometric transformation matrix linking the coordinates of the reference patterns with the coordinates of the channels, an identification step of the projected pattern in the alignment radiographic image of each channel, a matching step of the projected patterns in the alignment radiographic image respectively with the channels of the plate, a calculation step of parameters of a second geometric transformation matrix linking the coordinates of the projected patterns in the alignment radiographic image with the coordinates of the reference patterns, the position of the receiver unit being determined from the parameters of the first and second matrices.

The calculation step can further comprise calculating angles of orientation of the receiver unit from the parameters of the first and second matrices.

BRIEF DESCRIPTION OF THE DRAWINGS

Other advantages and features will become more clearly apparent from the following description of particular embodiments and of implementation of the invention given for non-restrictive example purposes only and represented in the appended drawings, in which.

DETAILED DESCRIPTION

Figure 1:
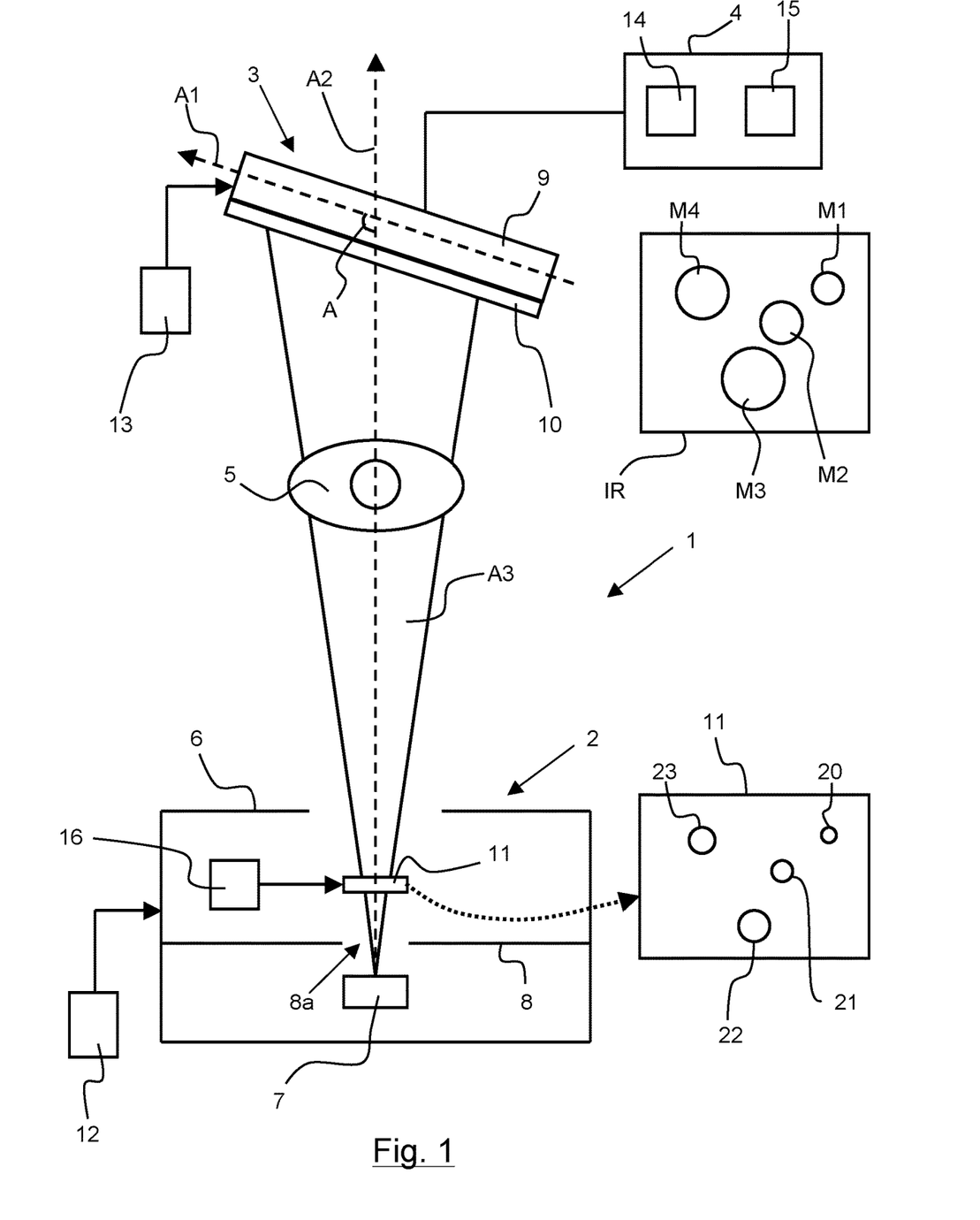
FIG. 1 schematically illustrates an embodiment of a radiographic imaging system according to the invention.

In FIG. 1, a radiographic imaging system 1 has been represented comprising an x-ray transmission unit 2, an x-ray receiver unit 3, a plate 11, and an image processing unit 4. The imaging system 1 is designed to make a radiographic image of an object 5, for example a patient, a bottle, or a part of a tube, and in particular an area of interest of the object 5 to be examined.

The transmission unit 2 can for example be an x-ray tube. The transmission unit 2 comprises a casing 6 in which an x-ray source 7 and a diaphragm 8 are housed. The diaphragm 8 delineates an irradiated area 8a generally having a rectangular, circular or octagonal shape. The diaphragm 8 can open and close to make the quantity of x-rays sent to the receiver unit 3 vary. The source 7 produces an x-ray radiation which passes through the irradiated area 8a of the diaphragm 8, in the direction of the receiver unit 3. The x-ray beam has been schematically represented by the reference A3. The receiver unit 3 comprises an x-ray detector 9, and can comprise an anti-scatter grid 10 to reduce the disused x-rays and to improve the contrast of the images. The grid 10 can be focused, i.e. it can comprise bars oriented towards a focal point, or be non-focused when it comprises parallel bars. The receiver unit 3 can be positioned so that the incidence of the x-rays is perpendicular to the receiver unit 3. In this case, a longitudinal axis A1 of the receiver unit 3 is perpendicular to an axis of propagation A2 of the emitted x-ray radiation. Furthermore, for certain examinations, an oblique incidence of the x-ray radiation can be used, and in this case the longitudinal axis A1 is inclined by an angle A different from 90° with respect to the axis of propagation A2. For example, the receiver unit 3 can be inclined to visualise certain areas of the object 5 which are masked when an x-ray incidence at 90° is used. Furthermore, the transmission unit 2 and receiver unit 3 are movable in translation and in rotation, and can be moved manually, or by movement means, respectively represented by the reference numerals 12 and 13. The movement means 12, 13 can be manual or automated micrometric actuators to move the transmission unit 2 and receiver unit 3 of the imaging system 1. As a variant, the transmission unit 2 can be moved in automated manner and the receiver unit 3 can be moved manually by an operator.

The processing unit 4 cooperates with the plate 11 so as to improve the alignment of the receiver unit 3 with respect to the transmission unit 2. What is meant by aligning the receiver unit 3 is the operation which consists in positioning and orienting the receiver unit 3 with respect to the transmission unit 2, or vice versa, so as to produce a usable radiographic image, i.e. an image having a contrast level which enables a user to visualize the areas of interest of the object 5 to be analyzed. In order to align the receiver unit 3 with respect to the transmission unit 2, the object 5 to be examined is placed between the receiver unit 3 and the transmission unit 2, and the plate 11 is then placed on the transmission unit 2, and a first radiographic image IR is made, noted alignment image. Making the alignment image IR consists in emitting an x-ray radiation, by the transmission unit 2, in the direction of the receiver unit 3, and in then detecting the x-ray radiation, by the receiver unit 3, to generate the alignment image IR. The alignment image IR obtained enables the position and orientation of the receiver unit 3 with respect to the transmission unit 2 to be determined. As the alignment image IR is made when the object 5 is placed between the receiver unit 3 and the transmission unit 2, it is advantageous to provide a plate 11 which limits the x-ray radiation received by the object 5 in the alignment step of the component parts 2, 3 of the imaging system 1. The plate 11 further has to enable a usable alignment image IR to be generated to determine the position and orientation of the receiver unit 3 precisely.

The plate 11 is made from a material opaque to x-rays, for example lead or tungsten. The plate 11 has for example a thickness of at least 3 mm to block almost all of the photons having an energy used in conventional radiology. The plate 11 is situated between the transmission unit 2 and receiver unit 3, on the path A3 of the x-rays emitted by the transmission unit 2. More particularly, the plate 11 is situated between the x-ray source 7 and receiver unit 3. The plate 11 is preferably mounted on the x-ray tube 2. For example, the plate 11 is housed in the casing 6 of the tube 2. Advantageously, the plate 11 is situated in the casing 6 so that the diaphragm 8 is placed between the plate 11 and x-ray source 7.

The plate 11 is designed to receive an x-ray radiation emitted by the transmission unit 2 in order to be able to align the receiver unit 3 with the transmission unit 2. The plate 11 comprises at least four channels 20 to 23. Each channel 20 to 23 enables a part of the x-rays emitted by the transmission unit 2 to pass through the channel 20 to 23. A channel 20 to 23 can be an opening, such as a hole or a slot, filled or not with a material transparent to x-rays. In all cases, the channels let the x-rays pass. For example, the plate 11 comprises only four channels 20 to 23, and the quantity of x-rays transmitted to the object 5 is thereby reduced. In general manner, the diameter of the channels 20 to 23 is smaller than the length of the plate 11. The diameter of at least one channel can be larger than that of the other channels of the plate 11. Preferentially, the plate 11 is situated perpendicularly to the axis of propagation A2 of the x-rays so that the channels 20 to 23 are oriented towards the source 7 to obtain a projection of the channels, in the alignment image IR, which is not deformed.

Figure 6:
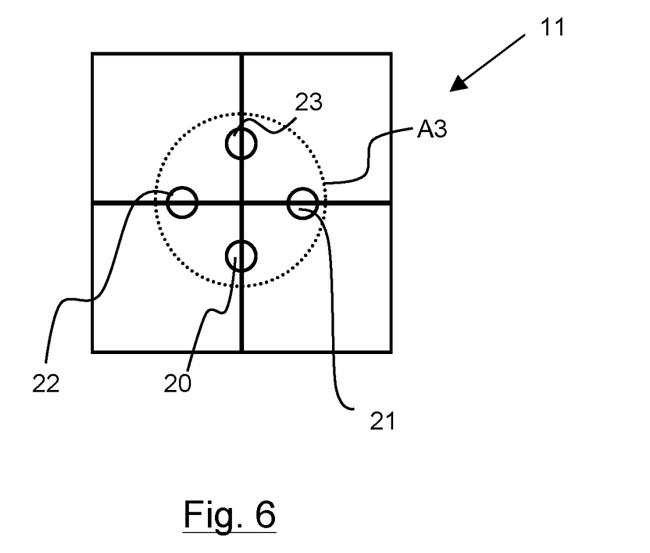
Figure 7:
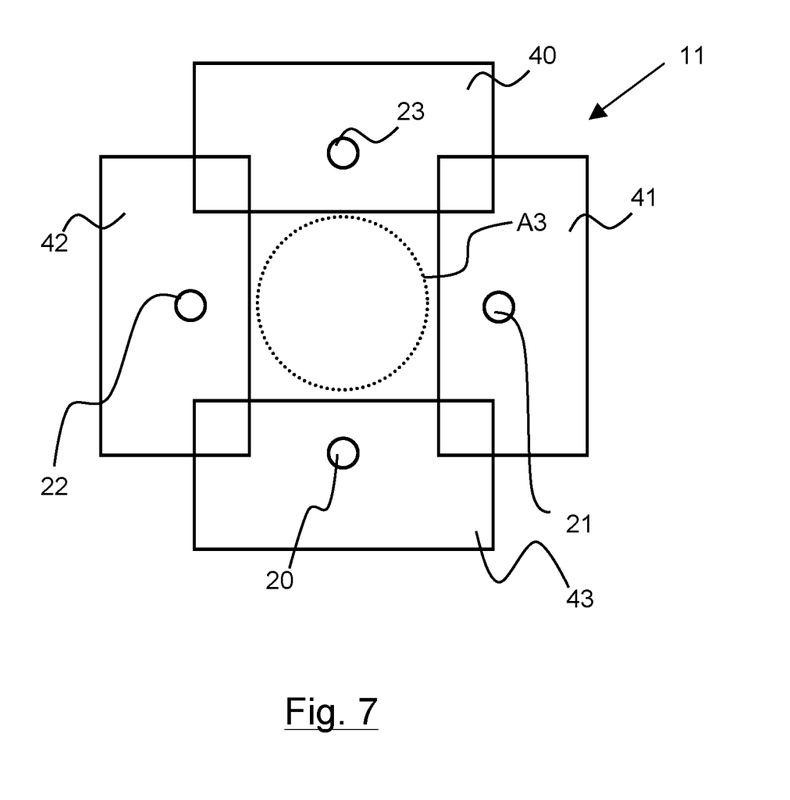
Figure 8:
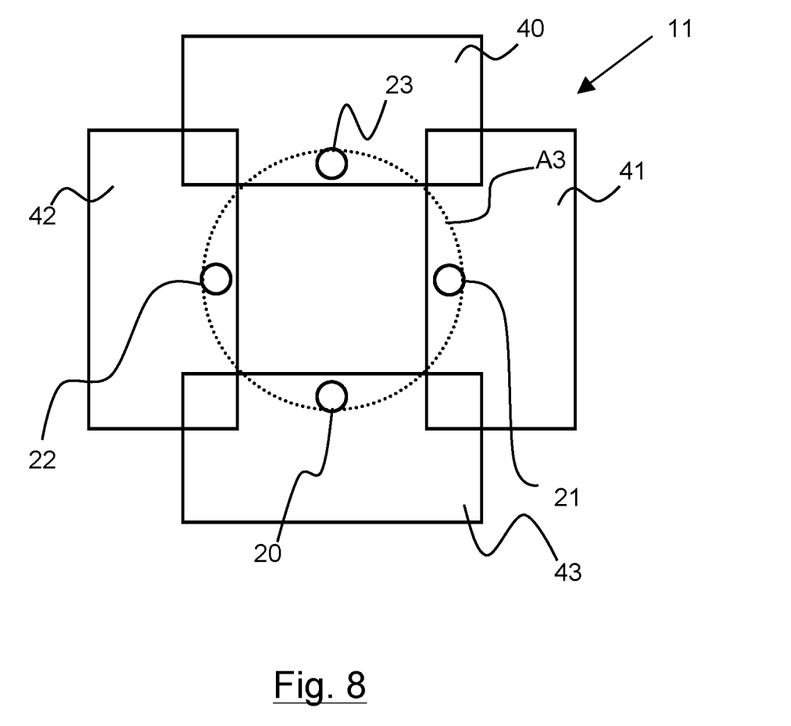

The plate 11 can comprise a single panel in which at least four channels 20 to 23 are formed. The plate 11 can also comprise several panels 40 to 43, each panel 40 to 43 comprising at least one channel among said at least four channels 20 to 23. Each panel 40 to 43 is made from a material opaque to x-rays. For example, the plate 11 can comprise two panels each having at least two channels 20 to 23. The plate 11 can comprise three panels at least one of which comprises at least two channels 20 to 23. The plate 11 can comprise four panels 40 to 43. The panels 40 to 43 can be mounted movable on the transmission unit 2 between a closed position in which the channels 20 to 23 are situated inside the x-ray beam A3, and an open position in which the channels 20 to 23 are situated outside the x-ray beam A3. In FIG. 6 a plate 11 with four panels 40 to 43 has been represented in a closed position, and in FIG. 7 the panels 40 to 43 have been represented in an open position. Thus, in the closed position, the alignment image IR can be generated. When the panels 40 to 43 are in the open position, a usable radiographic image of the object 5 can be produced. In particular, in the open position, the channels 20 to 23 can interact or not interact with the x-ray beam A3. It is advantageous for the channels 20 to 23 not to interact so as to reduce disturbances when making a radiographic image of the object 5. However as illustrated in FIG. 8, it may also be advantageous to leave the channels 20 to 23 in the beam when the panels are in the open position. The patterns formed by the channels enable additional checking of the radiographic image of the object 5. It is then possible to ensure that the receiver unit and transmission unit are correctly placed with respect to the object 5. It is then possible to detect and offset with respect to a previous positioning phase where the plates were in closed positions to generate the alignment image IR. In the open position, the x-ray flux is greater than in the closed position so as to take the radiographic image and not an alignment image.

The movable panels 40 to 43 make it possible to switch rapidly from the open position to the closed position, in other words to rapidly generate the alignment image IR and then the usable radiographic image of the object 5, and vice versa. For example the panels 40 to 43 are mounted movable in translation along axes perpendicular to the axis of propagation A2 (the axis of propagation A2 is perpendicular to the sheet plane of FIGS. 6 and 7) to move them away from one another to the open position and to move them towards one another to the closed position. In the closed position, the panels 40 to 43 can be in contact with one another or be partially juxtaposed with respect to one another, with or without contact between them. The plate 11 can be mounted on a transmission unit 2 which does not comprise a diaphragm 8.

Several embodiments of the plate 11 have been illustrated in FIGS. 2 to 6. In FIG. 1, a front view of the plate 11 has been represented comprising four channels 20 to 23, preferably four openings of circular cross-section, i.e. the channels 20 to 23 are of cylindrical shape. The channels 20 to 23 are located at specific positions in the plate 11 so that the figure formed by the four channels 20 to 23 is asymmetric. For example, the channels 20 to 23 are cylindrical and their cross-sections have different diameters from one another. In the example illustrated in FIG. 1, the channels 20 to 23 have the same cylindrical shape and have different diameters. The channels 20 to 23 are thus differentiated by their size.

According to another example, the channels 20 to 23 have the shape of a truncated cone. The apex of each truncated cone can be situated facing the x-ray source 7, their bases being situated facing the receiver unit 3. For example, the plate 11 can be situated in an optimal position with respect to the source 7, so that the apex of the truncated cones is situated on the axis of propagation A2 of the x-rays. The apex of the truncated cones is advantageously situated on the x-ray source 7.

Figure 2:
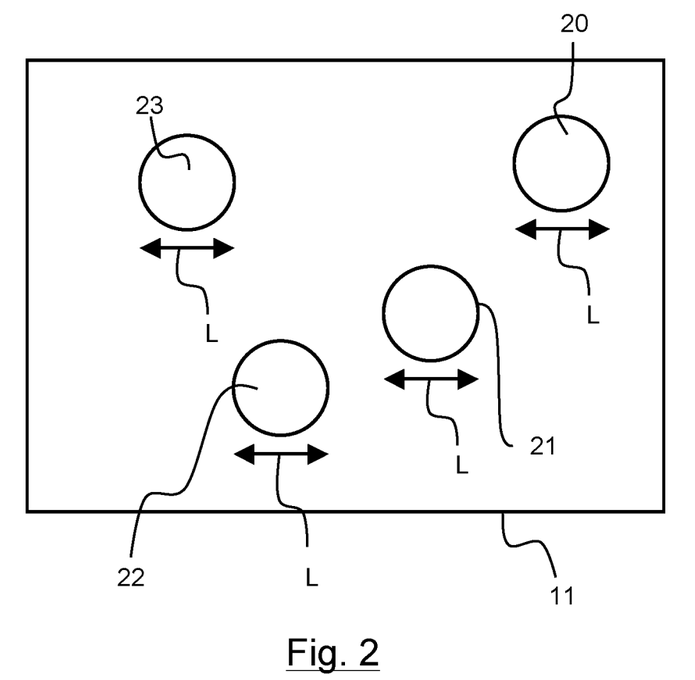
FIGS. 2 to 8 schematically illustrate embodiments of a plate according to the invention.

In FIG. 2, the plate 11 comprises four channels 20 to 23, in particular four openings of circular cross-section. The channels 20 to 23 are situated in specific positions in the plate 11 so that the figure formed by the four channels 20 to 23 is asymmetric. Furthermore, the channels 20 to 23 have a same length L, i.e. their cross-sections have the same diameter. The channels 20 to 23 are thus differentiated by their position on the plate 11.

Figure 3:
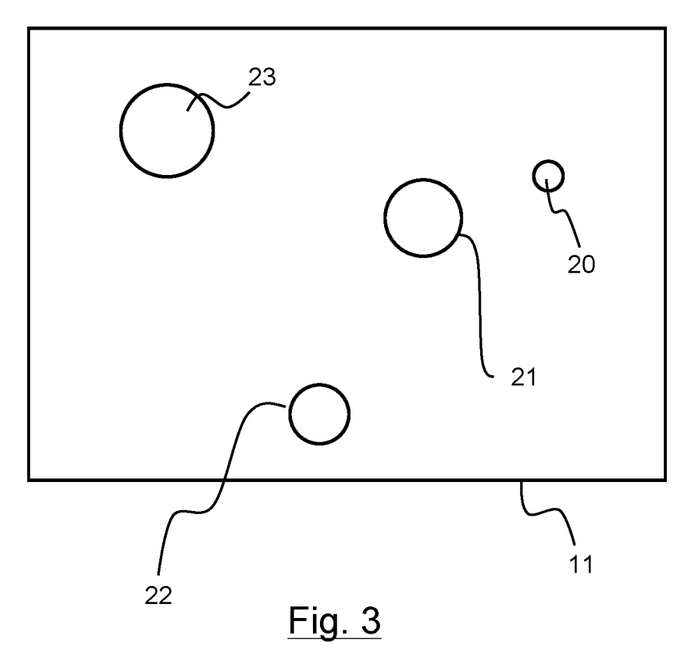

In FIG. 3, the plate comprises four cylindrical channels 20 to 23 arranged so as to form an asymmetric figure. Preferably, the distances separating the channels 20 to 23 are distinct so as to separate one channel 22 from the first two channels 20, 21. Preferentially, the arrangement of the channels 20 to 26 within the plate 11 forms an asymmetric figure. An asymmetric figure enables projected patterns of the channels which are situated at different distances from one another to be obtained in the alignment image IR. The different distances obtained will be able to facilitate matching of the projected patterns with the channels of the plate 11.

Figure 4:
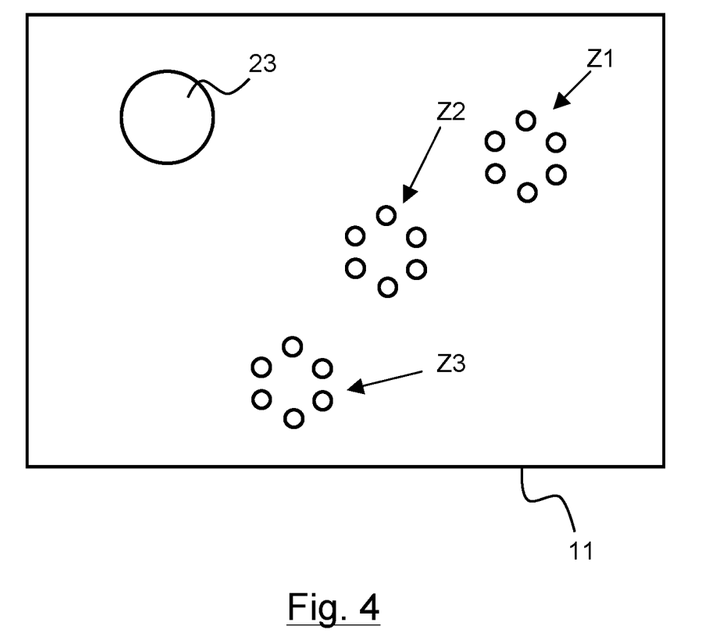

In FIG. 4, the plate 11 comprises three areas Z1 to Z3, each area comprising several channels, and a cylindrical channel 23 distinct from those of the areas. The three areas Z1 to Z3 each comprise six cylindrical channels arranged in symmetrical manner to form a circle. An area Z1 to Z3 comprising six channels enables the emitted x-ray dose to be reduced compared with a single channel surrounding the six channels. It can be noted that each area Z1 to Z3 forms a symmetric figure, however the arrangement of the areas Z1 to Z4 forms an asymmetric figure.

Figure 5:
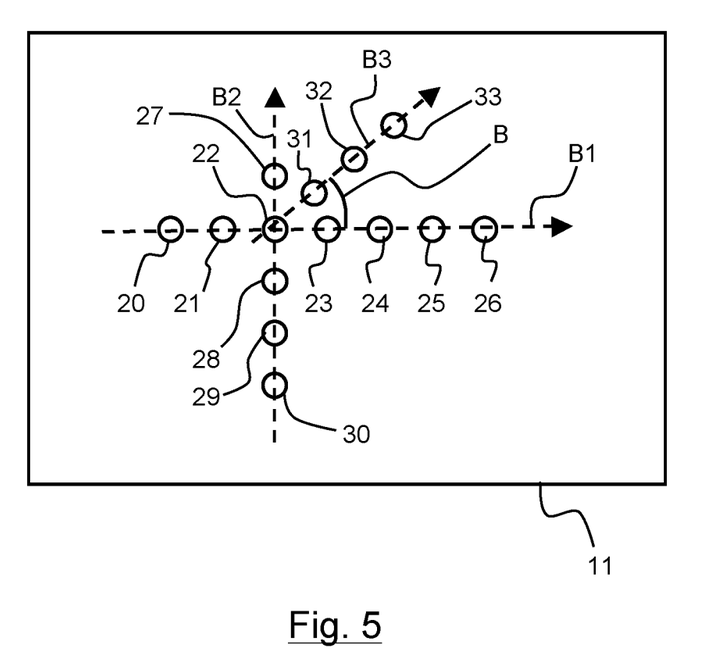

In FIG. 5, the plate 11 comprises fourteen channels 20 to 33. In particular, the plate 11 comprises a first group of seven channels 20 to 26 aligned along a first axis B1, a second group of four channels 27 to 30 aligned along a second axis B2 perpendicular to the first axis B1, and a third group of three channels 31 to 33 aligned along a third axis B3 inclined at an angle B with respect to the first and second axes B1, B2. Furthermore, the four channels 27 to 30 of the second group are aligned along the second axis B2 with the third channel 22 of the first group, starting from the left in FIG. 5. The three channels 31 to 33 of the third group are also aligned along the third axis B3 with the third channel 22 of the first group. For example, the angle B is equal to 45°. Each line of channels can comprise several channels. In this embodiment, the channels 20 to 33 have a circular cross-section and have the same diameter. In particular, the plate 11 comprises more than four channels when the transmission unit 2 is to be aligned with the receiver unit 3 in complex situations, for example in the case where the object 5 is bulky or when the x-ray radiation dosage is weak. In addition, aligning channels along three different axes B1 to B3 improves the ruggedness of the image processing by improving the determination of the coordinates of the projected patterns in the image.

The image processing unit 4 enables the position and orientation of the receiver unit 3 of the imaging system 1 to be determined. The image processing unit 4 is coupled to the receiver unit 3. The processing unit 4 is either integrated in the detector 9 or located outside the detector 9 being electrically connected to the detector 9 by a hard-wired or wireless link. The image processing unit 4 is for example a computer. The detector 9 receives the x-ray radiation emitted by the transmission unit 2 and generates an alignment radiographic image IR corresponding to the x-ray radiation received by the detector 9. The alignment image IR generated by the detector 9 comprises the respective projections of the channels 20 to 23 of the plate 11, i.e. the projected patterns M1 to M4 of the channels 20 to 23. Furthermore, the detector 9 transmits the generated images, by electric signal, to the processing unit 4 which determines the position and orientation of the receiver unit 3 with respect to the transmission unit 2. Determination of the position and orientation of the receiver unit 3 is performed from known image processing algorithms integrated in the processing unit 4. In general manner, the processing unit 4 determines the coordinates of the projected patterns M1 to M4 in the alignment image IR, and then determines a position of the receiver unit 3 from the determined coordinates and from the coordinates of the channels 20 to 23. The processing unit 4 can further also determine an inclination of the receiver unit 3 with respect to an axis perpendicular to the plate 11.

More particularly, the processing unit 4 comprises a memory to store parameters of a first geometric transformation matrix Kref. The geometric transformation associated to the first matrix Kref corresponds to a projection of the coordinates of the channels 20 to 23 of the plate 11 in a reference radiographic image. In other words, the first matrix Kref enables the coordinates of a projected pattern in the reference image to be linked with those of the channel 20 to 23 of the plate 11 which generated the projected pattern. The projected patterns in the reference image are also called reference patterns. The reference patterns are obtained by positioning the receiver unit 3 at a reference distance Dref from the receiver unit, and by generating the reference radiographic image of the plate 11. In particular, the receiver unit 3 is placed with a reference orientation in which the plane of the receiver unit 3 is parallel to the plane of the plate 11 and perpendicular to the axis of propagation A2 of the x-rays. The reference radiographic image is also generated with the plate 11 situated in the casing 6 of the transmission unit 2 and without an object 5 to be studied. The reference image thus comprises the respective projected patterns of the channels of the plate 11. The following relation can then be written, for a channel 20 to 23 of the plate 11 and for the projected pattern of the channel 20 to 23 in the reference radiographic image:

$$Qref = Kref \times P$$

with:
Kref: the first geometric transformation matrix;
P: a matrix of the coordinates of a channel 20 to 23 of the plate 11; and
Qref: a matrix of the coordinates of the reference pattern corresponding to the projection of the channel 20 to 23 in the reference radiographic image.

The processing unit 4 then determines the coordinates of a reference pattern and calculates the parameters of the first matrix Kref from the relation Qref=Kref×P, i.e. from the coordinates of the reference pattern, expressed by the matrix Qref, and from the coordinates of the channel associated with the reference pattern, expressed by the matrix P. The processing unit 4 can also calculate the parameters of the first matrix Kref, for each reference pattern and for each channel associated with the reference pattern, and compare the values of the parameters obtained for each calculation. To simplify the calculations, the coordinates of a point in a reference or alignment radiographic image are expressed according to a two-dimensional image coordinates system defined by two orthonormal vectors U, V and a point of origin O. The image coordinates system is linked to the reference and alignment radiographic images. A three-dimensional object coordinates system comprising three orthonormal vectors X, Y, Z and a point of origin I is also defined in which the coordinates of the channels are expressed. The object coordinates system is linked to the source 7. Furthermore, when the plate 11 is placed in the casing 6, the plate 11 is securely attached to the source 7, and the object coordinates system is also linked to the plate 11. The coordinates of the channels 20 to 23 of the plate 11 are expressed in the object coordinates system. The coordinates of the channels 20 to 23 are recorded beforehand in the memory of the processing unit 4. In general manner, the coordinates of a channel 20 to 23 correspond to the coordinates of the barycentre of a section of the channel 20 to 23. More particularly, the barycentre chosen to determine the coordinates of the channel 20 to 23 is the barycentre of a section of the channel situated at the level of the surface of the plate 11 placed facing the source 7. As a variant, the coordinates of a channel 20 to 23 correspond to the coordinates, expressed in the object coordinates system of a point representative of the channel 20 to 23. For example, the point representative of a channel 20 to 23 is located at the periphery of a section of the channel 20 to 23. According to another example, the point representative of a channel 20 to 23 is situated inside the channel 20 to 23, i.e. on a line linking the barycentre and a point located at the periphery of the section of the channel 20 to 23. Furthermore, the orientation of the plate 11 in the object coordinates system is also stored in the memory. Preferably, the plate 11 has an orientation at 90° with respect to the axis of propagation of the x-rays. For example, the matrix Kref can be written in the following manner:

$$Kref = \begin{bmatrix} k \times Dref & 0 & U0 \\ 0 & k \times Dref & V0 \\ 0 & 0 & 1 \end{bmatrix}$$

with:
Dref: the reference distance of the receiver unit 3, expressed in metres;
k: a conversion factor of metres into pixels, the value of which is a function of the type of detector 9 and the unit of which is in pixels per metre;
U0, V0: coordinates, in the image coordinates system, of a point of the reference image corresponding to the orthogonal projection of the x-ray source 7.

The other matrices can also be written in the following manner:

$$Qref = \begin{bmatrix} Um1 \\ Vm1 \\ 0 \end{bmatrix}$$

with
Um1, Vm1: the coordinates of a reference pattern in the image coordinates system; and $$P = \begin{bmatrix} Xc1 \\ Yc1 \\ Zc1 \end{bmatrix}$$

Xc1, Yc1, Zc1: the coordinates of a channel in the object coordinates system.

To determine the positioning of the receiver unit 3, the alignment image IR is generated with the same plate 11 for which the parameters of the first geometric transformation matrix Kref have been defined, and with the object 5 to be analyzed situated between the receiver unit 3 and the transmission unit 2. From the alignment radiographic image IR, the processing unit 4 identifies the projected patterns M1 to M4 in the alignment image IR by means of known image processing algorithms to detect the outlines of the projected patterns M1 to M4. The same algorithms can be applied to the reference image to identify the reference patterns. For example, Canny filters can be used. Segmentation algorithms by grey level thresholding can be previously applied to the alignment image IR to obtain a simplified image in order to improve the detection of the contours. In addition, filtering can be applied to the alignment image IR to eliminate the isolated pixels, i.e. to eliminate the image noise. Image processing algorithms configured to determine the characteristics of each projected pattern can then be applied in order to identify the patterns. The characteristics are in particular the shape, length and coordinates of the projected pattern in the alignment image IR. For example, a Hough transform function can be applied to determine the characteristics of the projected patterns M1 to M4. When the channels 20 to 23 are cylindrical, the projected patterns M1 to M4 are circles or ellipses. In this case, the coordinates of the pattern are those of the center of the circle or of the ellipse. In general manner, the coordinates of a pattern correspond to the coordinates of the barycentre of the pattern. As a variant, the coordinates of a projected pattern M1 to M4 correspond to the coordinates, expressed in the image coordinates system, of a point representative of the projected pattern M1 to M4. For example, the point representative of a projected pattern M1 to M4 is situated at the periphery of the projected pattern M1 to M4, i.e. situated on the contour of the projected pattern M1 to M4. According to another example, the point representative of a projected pattern M1 to M4 is situated inside the projected pattern M1 to M4, i.e. on a line linking the barycentre and a point situated on the contour of the projected pattern M1 to M4. The other characteristics of the patterns M1 to M4 are the diameters of the circles, the small and large axes of the ellipses. Then the processing unit 4 matches the identified patterns M1 to M4 with the associated channels 20 to 23 of the plate 11. In other words, the processing unit 4 matches the projected patterns M1 to M4 by means of a table of characteristics stored in the memory of the processing unit 4. For example, the table comprises the characteristics of the channels 20 to 23 of the plate 11, i.e. their shape, their length and their position in the plate 11. More particularly, matching consists in scrutinizing the alignment image IR to identify the projected patterns M1 to M4, and at each identified projected pattern, the processing unit 4 calculates the characteristics of the pattern, such as for example its shape, its length, and its position in the IR image. Then the processing unit 4 compares the calculated characteristics with those of the table and detects the channel of the plate which corresponds to the projected pattern. For example, a projected pattern corresponds to a channel of the plate when the calculated characteristics are proportional to those of the table. The proportionality corresponds to an enlargement or a shrinking, according to the position of the detector 9. Furthermore, when the channels 20 to 23 have the same size, for example the same diameter, matching is performed according to the position of the projected patterns in the image, as the position of the patterns in the image enable them to be differentiated from one another. On the contrary, when the channels have different sizes, matching is performed according to the sizes of the projected patterns, as they are different from one another.

Then, using known image processing algorithms, the processing unit 4 calculates parameters of a second geometric transformation matrix H linking the coordinates of the reference patterns with the coordinates of the projected patterns M1 to M4 in the alignment radiographic image IR. The second matrix H corresponds to a planar homography between the reference radiographic image and the alignment radiographic image IR. This planar homography is represented mathematically by the second matrix H. The following relation can be written for each projected pattern in the reference image:

$Q\text{ali} = H \times Q\text{ref}$ with:
H: the second geometric transformation matrix;

Qref: the matrix of the coordinates of the reference pattern corresponding to the projection of the channel 20 to 23 in the reference radiographic image;

Qali: a matrix of the coordinates of the pattern of the channel 20 to 23 projected in the alignment radiographic image.

The processing unit 4 calculates the parameters of the second matrix from the relation Qali=H×Qref, i.e. from the coordinates of a projected pattern in the alignment image, expressed by the matrix Qali, and from the coordinates of the associated reference pattern, expressed by the matrix Qref. The projected pattern in the alignment image and the associated reference pattern are generated by the same channel of the plate 11.

It is further possible to link the coordinates of a projected pattern M1 to M4 in the alignment image IR with the coordinates of the channel of the plate 11 which generated the projected pattern, from a third geometric transformation matrix Kali. The third geometric transformation associated with the third matrix Kali corresponds to a projection of the coordinates of a channel 20 to 23 of the plate 11 in the alignment image IR. In other words, the third matrix Kali enables the coordinates of a projected pattern in the alignment image IR to be linked with those of the channel 20 to 23 of the plate 11 which generated the projected pattern.

The following relation can further be written:

$$Q\text{ali} = K\text{ali} \times R\text{ali} \times P$$

with:

Kali: the third matrix corresponding to the third geometric transformation; and

Rali: a rotation matrix of the third geometric transformation.

From the relations described in the foregoing, the following relation is obtained:

$$K\text{ali} \times R\text{ali} = H \times K\text{ref}$$

For example, the third matrix Kali of the third geometric transformation can be written in the following manner:

$$K\text{ali} = \begin{bmatrix} k' \times D & 0 & U0 \\ 0 & k' \times D & V0 \\ 0 & 0 & 1 \end{bmatrix}$$

with:

k': another conversion factor of metres into pixels, the value of which is a function of the type of detector 9 and the unit of which is in pixels per metre;

D: the distance between the receiver unit 3 and the transmission unit 2, expressed in metres, when the alignment image IR is generated.

The processing unit 4 calculates the parameters of the matrices Kali and Rali from the product between the first and second matrices Kref, and H. Then the processing unit 4 calculates the position and orientation of the receiver unit from the calculated parameters. More particularly, the processing unit 4 calculates the distance D between the receiver unit 3 and the transmission unit 2. Furthermore, the rotation matrix Rali can be broken down into three matrices, i.e. three other matrices each representing a rotation of the receiver unit 3 with respect to an axis X, Y, Z of the object coordinates system.

The user can further enter, by means of a graphic interface 14, a position, or a distance between the transmission unit 2 and the receiver unit 3, and a required inclination. The processing unit 4 then calculates the difference of position between the required position and the determined position, and the difference of orientation between the required orientation and the determined orientation. By means of the calculated differences, the processing unit can provide position and orientation correction information.

Then, from the position and orientation correction information, the transmission unit 2 can be aligned with the receiver unit 3, in manual manner by an operator, or in automatic manner by means of movement means 12, 13 which can be motorized and controlled by the image processing unit 4. Furthermore, the imaging system 1 can comprise an indicating unit 15, for example a display, coupled to the processing unit 4 to indicate the determined position and orientation values to the operator. The indicating unit 15 can further indicate the initial distance determined by the processing unit 4. The indicating unit 15 can also indicate a movement information, in translation and in rotation, to align the transmission unit 2. Preferentially, the movement information corresponds to the movement of the transmission unit 2 necessary to align it with respect to the receiver unit 3. For example, the movement information is that which enables the transmission unit 2 to be moved so that the distance between the receiver unit 3 and the transmission unit 2 is equal to an optimal distance provided by the manufacturer of the receiver unit 3. The optimal distance can be the focal distance from the anti-scatter grid 10 in the case where the receiver unit 3 is equipped with such a grid. The casing 6 of the transmission unit 2 can further comprise movement means 16 to place and remove the plate 11 in automated manner.

When the receiver unit 3 and transmission unit 2 are aligned, the plate 11 is removed, and a normal radiographic image of the object 5 is made, noted diagnostic image.

In general manner, and to determine the position and inclination of the receiver unit 3, the projected patterns M1 to M4 of the alignment image IR have to have a minimum diameter of 1 mm. In this case, when an alignment image IR is to be made with the receiver unit 3 located at a distance from the transmission unit 2 for which the enlargement factor of the channels 20 to 23 of the plate 11 is equal for example to 10, a plate 11 will be made with channels having a diameter of more than 100 μm. Projected patterns M1 to M4 having a diameter of about 1 mm are thus obtained in the alignment image IR, which enables these patterns to be detected. When the receiver unit 3 has a smaller enlargement factor, for example for an imaging system used in the dental field for which the distances between the movable parts 2, 3 are reduced, a plate 11 able to have channels 20 to 23 having an identical shape is used, the diameter of each channel of which is however less than 100 μm. For example, the enlargement factor can be equal to 4 and the plate 11 used then has channels 20 to 23 each having a diameter equal to 50 μm. Depending on the radiographic detector use, the size of the channels is adjusted to the type of detector, in particular according to the size of the pixels.

In particular, the alignment image is made with a weak x-ray dose. This weak dose corresponds to about 10 times less than a normal dose to make a diagnostic radiographic image. Furthermore, the surface ratio between an irradiation field without a plate with open diaphragms, for example of 20 cm×20 cm, and the field surface with a plate where the x-rays only pass through the channels is about 10,000. For example, for a diagnostic radiographic image requiring a surface dose product SDP of about 100 cGy·cm2, the additional dose given to the patient during the alignment step is 10×10,000 times less, i.e. 10 microGy·cm2 in terms of SDP, which is negligible.

To achieve the dimensions and patterns of the channels, a succession of radiographic images are previously taken in the presence of calibrated objects and in the absence of a patient to be analyzed. A simulation is performed making the diameter of the channels vary, and the delivered x-ray dose necessary for detection of the projected patterns formed in the obtained radiographic images is recorded. The signal-to-noise ratio according to the size of the object 5 and the delivered dose can also be recorded. A set of plates 11 is then obtained respectively associated to different clinical situations, for example situations which require different x-ray doses. This set comprises plates 11 optimized to make a specific radiographic image from a given imaging system. The imaging system 1 enables a plate 11 to be placed according to the distance between the receiver unit and the transmission unit, and therefore according to the enlargement factor of the receiver unit 3. Other parameters can be taken into account, for example the thickness of the area of interest of the object 5, the sensitivity of the receiver unit 3, the contrast of the required image, etc.

A second alignment image can also be made to check the alignment of the receiver unit 3.

The positioning method of the receiver unit 3 with respect to the transmission unit, or vice versa, can be implemented by the imaging system 1 defined above. In an initial step, the receiver unit 3 and transmission unit 2 are arranged so that the object 5 to be analyzed is situated between the transmission unit 2 and detector 9.

The method further comprises the following steps:
arranging the plate 11 made from a material opaque to x-rays between the transmission unit 2 and receiver unit 3, the plate 11 comprising at least four channels 20 to 23, each channel enabling a part of the x-rays emitted by the transmission unit 2 to pass through the channel;
emitting x-rays by the transmission unit 2;
generating, by the receiver unit, an alignment radiographic image comprising a projected pattern of each channel;
determining coordinates of the projected patterns in the alignment radiographic image; and
calculating a position of the receiver unit 3 from the determined coordinates and from the coordinates of the channels.

Furthermore, prior to the alignment image generation step, a reference radiographic image can be generated so as to identify the geometric transformations to link the coordinates of the channels with the coordinates of projected patterns of the channels in the alignment image.

When emission of the x-ray radiation takes place, a weak dose is used, compared with the dose used to make a diagnostic radiographic image of the object 5.

A radiographic imaging system and a positioning method of the system are thus provided, minimizing the quantities of emitted x-rays and at the same time enabling distortion-free radiographic images to be made. Furthermore, the number of images taken is reduced in order to limit a patient's exposure to the x-rays. Such an imaging system is particularly suitable for environments comprising metal objects liable to disturb conventional remote-measurement electromagnetic systems.

The invention claimed is:
1. A radiographic imaging system comprising:
an x-ray transmission unit;
an x-ray receiver unit; and
a plate made from a material opaque to x-rays and situated between the transmission unit and the receiver unit,
wherein:
the plate comprises at least four channels, each channel enabling a part of the x-rays emitted by the transmission unit to pass through the channel;
the receiver unit generates an alignment radiographic image comprising a projected pattern of each channel;
the system comprises an image processing unit configured to determine the coordinates of the projected patterns in the alignment radiographic image, and to calculate a position of the receiver unit from the coordinates of the projected patterns in the alignment radiographic image and from the coordinates of the channels; and
the image processing unit comprises a memory to store parameters of a first geometric transformation matrix linking coordinates of reference patterns respectively with the coordinates of the channels, each reference pattern corresponding to a projection of a channel in a reference radiographic image generated when the receiver unit is located at a reference distance from the transmission unit, the image processing unit is further configured to identify the projected pattern in the alignment image of each channel, to match the projected patterns in the alignment radiographic image respectively with the channels of the plate, to calculate parameters of a second geometric transformation matrix linking the coordinates of the projected patterns in the alignment radiographic image with the coordinates of the reference patterns, and to calculate the position of the receiver unit from the parameters of the first and second matrices.

2. The system according to claim 1, wherein the plate comprises a single panel in which said at least four channels are formed.

3. The system according to claim 1, wherein the plate comprises at least two panels, each panel comprising at least one channel from said at least four channels.

4. The system according to claim 3, wherein the plate comprises four panels.

5. The system according to claim 4, wherein each panel comprises at least one channel from said at least four channels.

6. The system according to claim 3, wherein the transmission unit emits an x-ray beam in the direction of the receiver unit and the panels are mounted movable on the transmission unit between a closed position in which said at least four channels are situated inside the x-ray beam, and an open position in which said at least four channels are situated outside the x-ray beam.

7. The system according to claim 3, wherein the transmission unit emits an x-ray beam in the direction of the receiver unit and the panels are mounted movable on the transmission unit between a closed position in which said at least four channels are situated inside the x-ray beam, and an open position in which said at least four channels are situated inside the x-ray beam.

8. The system according to claim 1, wherein the plate comprises several channels forming an asymmetric figure.

9. The system according to claim 1, wherein the plate comprises at least two channels aligned along a first axis, at least two channels aligned along a second axis perpendicular to the first axis, and at least three channels aligned along a third axis inclined with respect to the first and second axes.

10. The system according to claim 1, wherein the transmission unit and the receiver unit are mobile.

11. The system according to claim 1, wherein the channels are of cylindrical shape.

12. The system according to claim 11, wherein the cross-sections of the channels have different diameters from one another.

13. A method for positioning a radiographic imaging system comprising an x-ray transmission unit and an x-ray receiver unit, comprising the following steps:
arranging a plate made from a material opaque to x-rays between the transmission unit and the receiver unit, the plate comprising at least four channels, each channel enabling a part of the x-rays emitted by the transmission unit to pass through the channel;
emitting x-rays by the transmission unit;
generating, by the receiver unit, an alignment radiographic image comprising a projected pattern of each channel;
determining coordinates of the projected patterns in the alignment radiographic image; and
calculating a position of the receiver unit from the coordinates of the projected patterns in the alignment radiographic image and from the coordinates of the channels, wherein
the calculation step comprises a calibration step in which generating a reference radiographic image comprising a projected reference pattern of each channel, by the receiver unit situated at a reference distance from the transmission unit, determining the coordinates of reference patterns, and calculating parameters of a first geometric transformation matrix linking the coordinates of the reference patterns with the coordinates of the channels, an identification step of the projected pattern in the alignment radiographic image of each channel, a matching step of the projected patterns in the alignment radiographic image respectively with the channels of the plate, a calculation step of parameters of a second geometric transformation matrix linking the coordinates of the projected patterns in the alignment radiographic image with the coordinates of the reference patterns, the position of the receiver unit being determined from the parameters of the first and second matrices.

14. The method according to claim 13, wherein the plate comprises at least two panels mounted movable on the transmission unit, each panel comprising at least one channel from said at least four channels, the transmission unit emits an x-ray beam in the direction of the receiver unit, and, when generating the alignment radiographic image, the panels are moved to a closed position in which said at least four channels are situated inside the x-ray beam, and the panels are moved to an open position in which said at least four channels are situated outside the x-ray beam to generate a diagnostic radiographic image of an object situated between the transmission unit and the receiver unit.

15. The method according to claim 13, wherein the plate comprises at least two panels mounted movable on the transmission unit, each panel comprising at least one channel from said at least four channels, the transmission unit emits an x-ray beam in the direction of the receiver unit, and, when generating the alignment radiographic image, the panels are moved to a closed position in which said at least four channels are situated inside the x-ray beam, and the panels are moved to an open position in which said at least four channels are situated inside the x-ray beam to generate a diagnostic radiographic image of an object situated between the transmission unit and the receiver unit.

16. The method according to claim 13, wherein the calculation step comprises calculating angles of orientation of the receiver unit from the parameters of the first and second matrices.

17. The method according to claim 13, wherein the plate comprises at least four panels, each panel comprising at least one channel from said at least four channels.

* * * * *